(12) United States Patent
Chen et al.

(10) Patent No.: US 9,484,193 B2
(45) Date of Patent: Nov. 1, 2016

(54) AUTOMATIC AMINO ACID SEQUENCING OF GLYCOPEPTIDE BY Y1 IONS

(71) Applicant: Academia Sinica, Taipei (TW)

(72) Inventors: Chung-Hsuan Chen, Taipei (TW);
Chein-Hung Chen, New Taipei (TW);
Hsin Yu Hsieh, Taipei (TW);
Pang-Hung Hsu, Taipei (TW);
Jung-Lee Lin, Banqiao (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/298,911

(22) Filed: Jun. 7, 2014

(65) Prior Publication Data
US 2015/0160232 A1 Jun. 11, 2015

(30) Foreign Application Priority Data
Dec. 9, 2013 (TW) .............................. 102145289 A

(51) Int. Cl.
*H01J 49/00* (2006.01)
*G01N 33/68* (2006.01)

(52) U.S. Cl.
CPC ....... *H01J 49/0031* (2013.01); *G01N 33/6818* (2013.01); *G01N 33/6851* (2013.01); *H01J 49/0054* (2013.01)

(58) Field of Classification Search
USPC ................................................ 250/282, 288
See application file for complete search history.

(56) References Cited

U.S. PATENT DOCUMENTS

| | | | | |
|---|---|---|---|---|
| 2009/0194684 A1* | 8/2009 | Guna | .................... | H01J 49/426 250/282 |
| 2010/0311176 A1* | 12/2010 | Williamson | ....... | G01N 33/6848 436/86 |
| 2011/0049351 A1* | 3/2011 | Zabrouskov | ....... | G01N 33/6848 250/282 |

OTHER PUBLICATIONS

Zaneer M. Segu and Yehia Mechref, "Characterizing protein glycosylation sites through higher-energy C-trap dissociation", Jan. 2010, Wiley InterScience, 24: 1217-1225.*
Zaneer M. Segu and Yehia Mechref, "Characterizing protein glycosylation sites through higher-energy C-trap dissociation", Jan. 2010, Wiley InterScience, 24; 1217-1225.*

* cited by examiner

*Primary Examiner* — Phillip A Johnston
*Assistant Examiner* — Hsien Tsai
(74) *Attorney, Agent, or Firm* — Eckman Basu LLP

(57) ABSTRACT

Apparatus and methods for automatic amino acid sequencing of a glycopeptide by mass spectrometry. The glycopeptide is fragmented by higher energy collision dissociation fragmentation, and sequentially fragmented by collision induced dissociation fragmentation. The glycopeptide Y1 ion is isolated, and the mass spectra of fragmented glycopeptide Y1 ions provide mass spectral peaks corresponding to the amino acid sequence of the glycopeptide.

13 Claims, 10 Drawing Sheets

SEQUENCE LISTING

```
<160> NUMBER OF SEQ ID NOS: 26

<210> SEQ ID NO 1
<211> LENGTH: 15
<212> TYPE: PRT
<213> ORGANISM: Bos taurus

<400> SEQUENCE: 1

Leu Cys Pro Asp Cys Pro Leu Leu Ala Pro Leu Asn Asp Ser Arg
1               5                   10                  15

<210> SEQ ID NO 2
<211> LENGTH: 15
<212> TYPE: PRT
<213> ORGANISM: Bos taurus

<400> SEQUENCE: 2

Thr Pro Ile Val Gly Gln Pro Ser Ile Pro Gly Gly Pro Val Arg
1               5                   10                  15

<210> SEQ ID NO 3
<211> LENGTH: 6
<212> TYPE: PRT
<213> ORGANISM: Bos taurus

<400> SEQUENCE: 3

Ala Asn Cys Ser Val Arg
1               5

<210> SEQ ID NO 4
<211> LENGTH: 11
<212> TYPE: PRT
<213> ORGANISM: Bos taurus

<400> SEQUENCE: 4

Asp Pro Thr Pro Leu Ala Asn Cys Ser Val Arg
1               5                   10

<210> SEQ ID NO 5
<211> LENGTH: 8
<212> TYPE: PRT
<213> ORGANISM: Bos taurus

<400> SEQUENCE: 5

Leu Ala Pro Leu Asn Asp Ser Arg
1               5
```

<210> SEQ ID NO 6
<211> LENGTH: 14
<212> TYPE: PRT
<213> ORGANISM: Bos taurus

<400> SEQUENCE: 6

Cys Pro Asp Cys Pro Leu Leu Ala Pro Leu Asn Asp Ser Arg
1               5                   10

<210> SEQ ID NO 7
<211> LENGTH: 9
<212> TYPE: PRT
<213> ORGANISM: Bos taurus

<400> SEQUENCE: 7

Asn Ala Glu Ser Asn Gly Ser Tyr Leu
1               5

<210> SEQ ID NO 8
<211> LENGTH: 16
<212> TYPE: PRT
<213> ORGANISM: Bos taurus

<400> SEQUENCE: 8

Asn Ala Glu Ser Asn Gly Ser Tyr Leu Gln Leu Val Glu Ile Ser Arg
1               5                   10                  15

<210> SEQ ID NO 9
<211> LENGTH: 15
<212> TYPE: PRT
<213> ORGANISM: Bos taurus

<400> SEQUENCE: 9

Gly Glu Asn Ala Thr Val Asn Gln Arg Pro Ala Asn Pro Ser Lys
1               5                   10                  15

<210> SEQ ID NO 10
<211> LENGTH: 17
<212> TYPE: PRT
<213> ORGANISM: Bos taurus

<400> SEQUENCE: 10

Thr Glu Glu Leu Gln Gln Gln Asn Thr Ala Pro Thr Asn Ser Pro Thr
1               5                   10                  15

Lys

<210> SEQ ID NO 11
<211> LENGTH: 16
<212> TYPE: PRT
<213> ORGANISM: Homo sapiens

<400> SEQUENCE: 11

Cys Ala Asn Leu Val Pro Val Pro Ile Thr Asn Ala Thr Leu Asp Arg
1               5                   10                  15

<210> SEQ ID NO 12
<211> LENGTH: 6
<212> TYPE: PRT
<213> ORGANISM: Homo sapiens

<400> SEQUENCE: 12

Asn Glu Glu Tyr Asn Lys
1               5

<210> SEQ ID NO 13
<211> LENGTH: 14
<212> TYPE: PRT
<213> ORGANISM: Homo sapiens

<400> SEQUENCE: 13

Tyr Phe Thr Pro Asn Lys Thr Glu Asp Thr Ile Phe Leu Arg
1               5                   10

<210> SEQ ID NO 14
<211> LENGTH: 15
<212> TYPE: PRT
<213> ORGANISM: Homo sapiens

<400> SEQUENCE: 14

Gln Asp Gln Cys Ile Tyr Asn Thr Thr Tyr Leu Asn Val Gln Arg
1               5                   10                  15

<210> SEQ ID NO 15
<211> LENGTH: 7
<212> TYPE: PRT
<213> ORGANISM: Homo sapiens

<400> SEQUENCE: 15

Glu Asn Gly Thr Ile Ser Arg
1               5

<210> SEQ ID NO 16
<211> LENGTH: 13
<212> TYPE: PRT
<213> ORGANISM: Armoracia rusticana

<400> SEQUENCE: 16

Tyr Asp Asn Ser Cys Pro Asn Val Ser Asn Ile Val Arg
1               5                   10

<210> SEQ ID NO 17
<211> LENGTH: 12
<212> TYPE: PRT
<213> ORGANISM: Armoracia rusticana

<400> SEQUENCE: 17

Asp Asn Ser Cys Pro Asn Val Ser Asn Ile Val Arg
1               5                   10

<210> SEQ ID NO 18
<211> LENGTH: 21
<212> TYPE: PRT
<213> ORGANISM: Armoracia rusticana

<400> SEQUENCE: 18

Leu Asp Asn Thr Thr Ser Phe Arg Thr Glu Lys Asp Ala Phe Gly Asn
1               5                   10                  15

Ala Asn Ser Ala Arg
            20

<210> SEQ ID NO 19
<211> LENGTH: 8
<212> TYPE: PRT
<213> ORGANISM: Armoracia rusticana

<400> SEQUENCE: 19

Leu Asp Asn Thr Thr Ser Phe Arg
1               5

<210> SEQ ID NO 20
<211> LENGTH: 17
<212> TYPE: PRT
<213> ORGANISM: Armoracia rusticana

<400> SEQUENCE: 20

Asp Ser Phe Arg Asn Val Gly Leu Asn Arg Ser Ser Asp Leu Val Ala
1               5                   10                  15

Leu

<210> SEQ ID NO 21
<211> LENGTH: 13
<212> TYPE: PRT
<213> ORGANISM: Armoracia rusticana

<400> SEQUENCE: 21

Asn Val Gly Leu Asn Arg Ser Ser Asp Leu Val Ala Leu
1               5                   10

<210> SEQ ID NO 22
<211> LENGTH: 23
<212> TYPE: PRT
<213> ORGANISM: Armoracia rusticana

<400> SEQUENCE: 22

Gly Leu Ile Gln Ser Asp Gln Glu Leu Phe Ser Ser Pro Asn Ala Thr
1               5                   10                  15

Asp Thr Ile Pro Leu Val Arg
            20

<210> SEQ ID NO 23
<211> LENGTH: 14
<212> TYPE: PRT
<213> ORGANISM: Armoracia rusticana

<400> SEQUENCE: 23

Phe Ser Ser Pro Asn Ala Thr Asp Thr Ile Pro Leu Val Arg
1               5                   10

<210> SEQ ID NO 24
<211> LENGTH: 13
<212> TYPE: PRT
<213> ORGANISM: Armoracia rusticana

<400> SEQUENCE: 24

Ser Ser Pro Asn Ala Thr Asp Thr Ile Pro Leu Val Arg
1               5                   10

<210> SEQ ID NO 25
<211> LENGTH: 21
<212> TYPE: PRT
<213> ORGANISM: Armoracia rusticana

<400> SEQUENCE: 25

Val Glu Ala Met Asp Arg Met Gly Asn Ile Thr Pro Leu Thr Gly Thr
1               5                   10                  15

Gln Gly Gln Ile Arg
            20

<210> SEQ ID NO 26
<211> LENGTH: 15

```
<212> TYPE: PRT
<213> ORGANISM: Armoracia rusticana

<400> SEQUENCE: 26

Met Gly Asn Ile Thr Pro Leu Thr Gly Thr Gln Gly Gln Ile Arg
1               5                   10                  15
```

AUTOMATIC AMINO ACID SEQUENCING OF GLYCOPEPTIDE BY Y1 IONS

SEQUENCE LISTING

This application includes a Sequence Listing submitted electronically herewith as an ASCII file created on Aug. 2, 2014, named ASN744US_SL.txt, which is 5,129 bytes in size, and is hereby incorporated by reference in its entirety.

BACKGROUND OF THE INVENTION

Glycosylation is a post-translational modification of proteins in cells. Glycans are linked to amino acids through glycosidic bonds. N-type linkages to asparagine and O-type linkages to serine and threonine are predominant forms. Protein glycosylation is involved in cellular activities, such as protein folding, immune response, and cell to cell communication. Abnormal glycosylation can play a role in cancer cell growth and metastasis.

Glycosylation sites and glycan structures can be determined in part by enrichment of glycopeptides, or by enzymatically or chemically releasing glycans. The structure of released glycans and remaining peptides can be determined by mass spectrometry and liquid chromatography/mass spectrometry. Fragmentation techniques can also be used to obtain glycan structures and amino acid sequences of the peptide backbone of glycopeptides with mass spectrometry. For example, glycosidic linkage obtained from collision induced dissociation may be combined with peptide sequence from electron-transfer dissociation to identify glycosylation sites and glycan structures of glycoproteins.

A drawback of these methods is low fragmentation efficiency of glycopeptides. Because of the structural complexity of glycans in glycopeptides, fragmentation techniques can be inefficient and time-consuming due to the need for manual data analysis from multiple experiments.

Further, a mass spectrometer for such analysis should have the ability, in a single result, to provide sequential collision-induced mass spectral analysis, so that multiple experiments would not be needed.

Moreover, a mass spectrometer for such analysis should have the ability to provide uniform collisional energies for glycopeptide fragmentation, regardless of glycopeptide structure, so that the analysis can be applied to a wide range of structures.

What is needed are methods and apparatus for accurate and efficient analysis of glycoproteins by mass spectrometry.

There is a continuing need for a mass spectrometer apparatus for analysis of glycopeptides, in a single mass spectrometric result, for identifying glycosylation sites, determining amino acid sequences, and other features.

BRIEF SUMMARY

This invention relates to the fields of proteomics and protein characterization. More particularly, this invention relates to methods and devices for mass spectrometry for glycopeptide analysis, including glycosylation sites, composition and amount of glycans, and automatic glycopeptide sequencing.

This invention provides methods and apparatus for mass spectrometry in proteomics and protein characterization, including glycopeptide analysis. The methods and apparatus of this invention can be used for identifying glycosylation sites, determining the composition and amount of glycans, and for automatic glycopeptide amino acid sequencing.

This invention provides a comprehensive method, in one mass spectrometric analysis of a glycopeptide, to identify glycosylation sites, determine amino acid sequences, reveal sugar compositions of the corresponding glycans, and measure the relative amounts of different glycans.

Embodiments of this invention include a mass spectrometry apparatus that can measure, in a single result, a full range mass spectrum, a first sequential collision induced mass scan, and a second sequential collision induced mass scan.

Embodiments of this invention include:

A mass spectrometer apparatus for glycopeptide analysis comprising:
an ionization source for creating glycopeptide analyte ions;
a quadrupole ion trap;
a linear ion trap;
a collision chamber between the quadrupole ion trap and the linear ion trap; and
a detector;
wherein the glycopeptide analyte ions exit the quadrupole ion trap into the collision chamber, thereby forming glycopeptide Y1 ions and product ions, and
wherein the linear ion trap performs mass analysis of glycopeptide Y1 ions and product ions created by higher energy collision dissociation fragmentation or collision induced dissociation fragmentation of the glycopeptide analyte ions that have exited the quadrupole ion trap.

The mass spectrometer apparatus above, wherein the higher energy collision dissociation fragmentation has a normalized collision energy from 70% to 110%, based on 100 V kinetic energy as being 100% high collision energy for an m/z of 2000.

The mass spectrometer apparatus above, wherein the ion source includes MALDI and ESI sources.

The mass spectrometer apparatus above, wherein the ion source includes an ESI source with a pulsed beam.

The mass spectrometer apparatus above, including an ion guide between the ion source and the quadrupole ion trap.

The mass spectrometer apparatus above, wherein the quadrupole ion trap is a mass analyzer.

The mass spectrometer apparatus above, wherein the linear ion trap is a mass analyzer.

A method for automatic amino acid sequencing of a glycopeptide, the method comprising:
obtaining the full mass range mass spectrum of glycopeptide analyte ions in a quadrupole ion trap;
selecting target glycopeptide ions from the full mass range mass spectrum and isolating the target glycopeptide ions in the quadrupole ion trap;
fragmenting the target glycopeptide ions by higher energy collision dissociation fragmentation, thereby obtaining fragmented glycopeptide analyte ions and glycopeptide Y1 ions;
obtaining the mass spectrum of the fragmented glycopeptide analyte ions and glycopeptide Y1 ions in the linear quadrupole ion trap, thereby identifying the glycopeptide Y1 ions;
isolating the glycopeptide Y1 ions in the linear ion trap;
fragmenting the glycopeptide Y1 ions in the linear ion trap by collision induced dissociation fragmentation;
obtaining the mass spectrum of the fragmented glycopeptide Y1 ions in the linear ion trap, thereby providing mass spectral peaks corresponding to the amino acid sequence of the glycopeptide.

The method above, wherein the normalized collision energy in the higher energy collision dissociation fragmentation step is set from 70% to 110%, based on 100 V kinetic energy as being 100% high collision energy for an m/z of 2000.

The method above, wherein the mass range of the linear ion trap is set to m/z greater than 800.

The method above, further comprising analyzing the mass spectral peaks corresponding to the amino acid sequence of the glycopeptide for a matching structure in a database of collision induced dissociation mass spectra.

The method above, wherein the glycopeptide is an O-linked glycopeptide or an N-linked glycopeptide.

The method above, wherein the linear ion trap is operable for mass analysis by voltage scan and frequency scan.

A method for determining the glycoform of a glycopeptide, the method comprising:

obtaining the $MS^1$ mass spectrum of glycopeptide precursor ions in a mass spectrometer as described above;

fragmenting the glycopeptide precursor ions to obtain glycopeptide product ions;

obtaining the $MS^3$ mass spectrum of glycopeptide product ions in a mass spectrometer as described above;

determining the amino acid sequence of the glycopeptide from the $MS^3$ mass spectrum;

determining the molecular weights of the glycans of the glycopeptide from the glycopeptide precursor ions and the determined amino acid sequence.

The method above, including resolving the sugar composition of the glycopeptide from the determined molecular weights of the glycans.

DETAILED DESCRIPTION OF THE INVENTION

Figure 1:
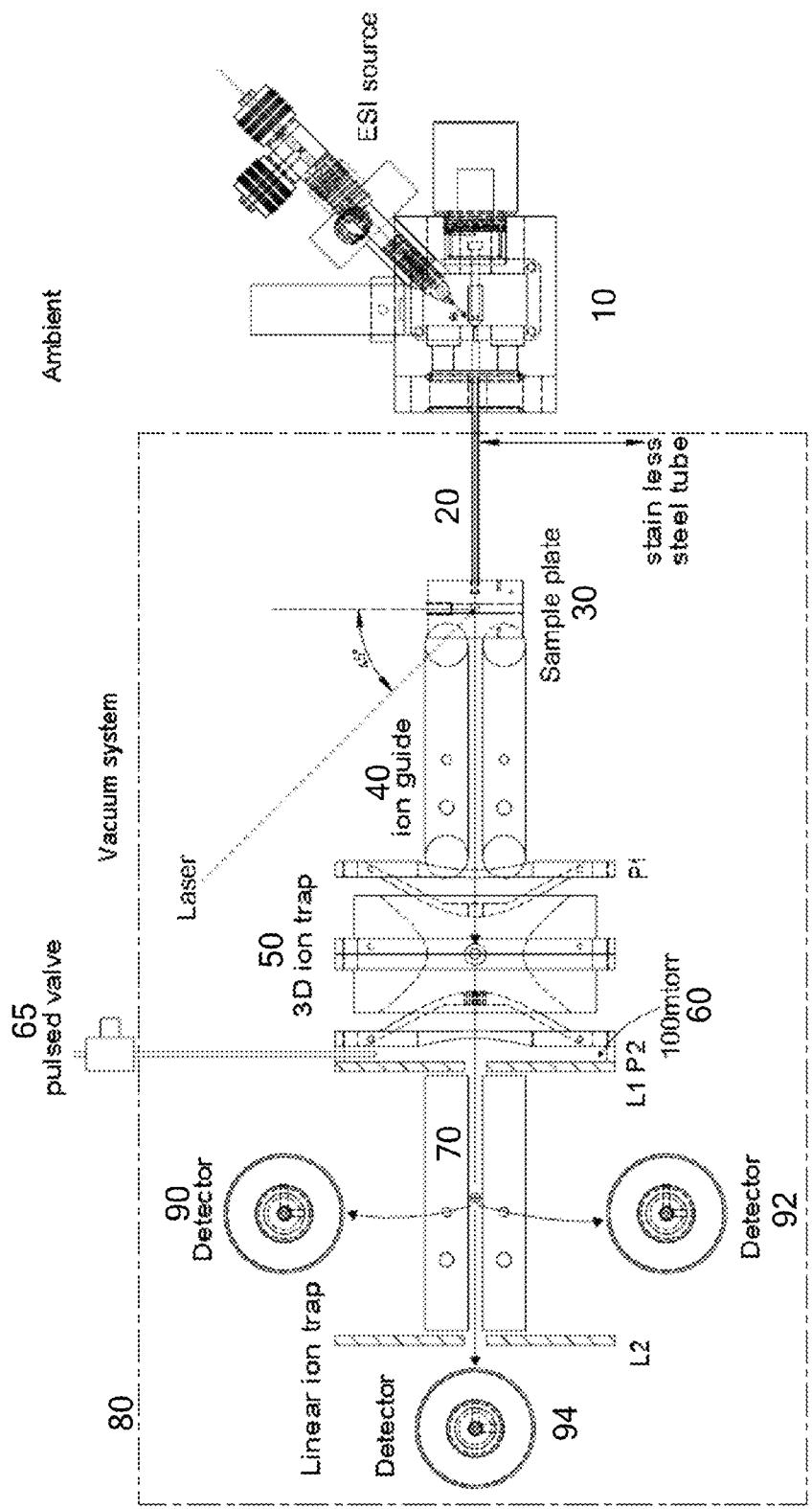
FIG. 1 shows a schematic of an embodiment of a mass spectrometer apparatus of this invention. The mass spectrometer apparatus can include an ion source 10, an ion transfer tube 20, a sample plate 30, an ion guide 40, a quadrupole ion trap 50, a collision and acceleration chamber 60, a pulsed valve 65, a linear ion trap 70, a vacuum enclosure 80, a first radial ion detector 90, a second radial ion detector 92, and an axial ejection detector 94.

This invention provides apparatus and methods for mass spectrometry in proteomics and protein characterization. More particularly, this invention provides a mass spectrometry apparatus and methods for glycopeptide analysis.

The methods and apparatus of this invention can be used for identifying glycosylation sites in glycopeptides, as well as determining the composition and amount of glycans in glycopeptides.

In some embodiments, the methods and apparatus of this invention can provide automatic glycopeptide amino acid sequencing.

In certain aspects, this invention provides a comprehensive method, in one mass spectrometric analysis of a glycopeptide, to identify glycosylation sites, determine amino acid sequences, reveal sugar compositions of the corresponding glycans, and measure the relative amounts of different glycans.

Embodiments of this invention include a mass spectrometer apparatus that can measure, in a single result, a full range mass spectrum, a first sequential collision induced mass scan, and a second sequential collision induced mass scan.

Embodiments of this invention provide methods and apparatus for Automatic Glycopeptide Sequencing by its Y1 ion (AGSY).

The glycopeptide Y1 ion comprises the glycopeptide plus one monosaccharide glycan, usually N-acetylglucosamine (GlcNAc), and is singly charged.

The automatic glycopeptide sequencing of this invention utilizes a universal setup of instrumental parameters, which is applicable for both N- and O-type glycopeptides with different amino acid sequences as well as different glycan structures.

The glycopeptide Y1 ions (for N-linked glycopeptides) and peptide ions (for O-linked glycopeptides) can be automatically identified in MS2 and sequentially performed to MS3 for peptide backbone fragmentation of glycopeptides.

Mass Spectometer Apparatus

Embodiments of this invention provide a dual ion trap mass spectrometer that can be used for automatic glycopeptide sequencing and other characterization of glycoproteins.

A dual ion trap mass spectrometer of this invention may have a quadrupole ion trap for providing a full mass analysis of a protein, as well as a linear ion trap. The linear ion trap may also be used as a mass analyzer. The linear ion trap can also be used to perform fragmentation of the protein, for additional mass analysis.

In further embodiments, the linear ion trap can perform higher energy collision dissociation fragmentation (HCD).

In some embodiments, the linear ion trap can perform collision induced dissociation fragmentation (CID).

Examples of a quadrupole ion trap include a Paul trap.

Examples of a linear ion trap include an LTQ trap.

Embodiments of this invention can overcome the drawbacks of conventional methods by providing a three-stage apparatus and process for obtaining the mass spectra of glycoproteins.

The collision energy applied for fragmentation of a glycoprotein in a mass spectrometer is related to the charge state and the m/z value of the precursor ion. It is necessary to determine the charge states of the precursor ions, so that adequate collision energy can be applied for any glycoprotein structure.

The methods and apparatus of this invention provide the surprising result that a fixed collision energy can be applied for adequate fragmentation of any glycoprotein structure. This surprising result allows, among other things, the advanced methods and apparatus for automatic glycopeptide sequencing of this invention.

The automatic glycopeptide sequencing methods of this invention can be achieved with an inventive apparatus of this disclosure, which provides detection of a three-stage mass spectrum.

In some embodiments, the first stage of data acquisition can be a full mass range scan ($MS^1$) of the glycopeptide. In a second stage, data acquisition can be a mass analysis scan ($MS^2$) obtained after higher energy collisional dissociation of the glycopeptide. In a third stage, data acquisition can be a mass analysis scan ($MS^3$) obtained after collision induced dissociation of the glycopeptide Y1 ion.

In addition to providing automatic glycopeptide sequencing, embodiments of this invention may further provide the identification of glycosylation sites of the glycopeptide, as well as a determination of the glycan structures for each glycosylation site.

In some embodiments, the unique arrangement of the mass spectrometer apparatus of this invention, more specifically, the arrangement of a quadrupole ion trap and linear ion trap with a collision chamber in between, allows sequential detection of fragment-$MS^2$ and fragment-$MS^3$ in the same experiment. This arrangement advantageously provides the simultaneous identification of glycopeptide Y1 ions in $MS^2$ and the determination of the amino acid sequence of the peptide in the sequential $MS^3$.

In general, higher energy collisional dissociation can be used for glycosidic bond cleavage. The fragmentation of glycosidic bonds with collision energy may result in the formation of glycopeptide Y1 ion, which is peptide with one GlcNAc, and oxonium ions, instead of b(M−OH) and y(M+H) ions.

The glycopeptide Y1 ions can be isolated, and a subsequent tandem mass spectrum of glycopeptide Y1 ions can provide amino acid sequences of the glycopeptide.

Embodiments of this invention provide a dual ion trap mass spectrometer that can be used to sequentially obtain a higher energy collision dissociation fragmentation mass spectrum ($MS^2$), and a collision induced dissociation fragmentation mass spectrum ($MS^3$) in the same experiment.

An inventive apparatus and method of this disclosure allows simultaneous identification of glycopeptide Y1 ions in mass spectrum $MS^2$ and determination of the amino acid sequence of peptide in a sequential mass spectrum $MS^3$.

In general, the collision energy required to observe the maximum signal intensity of a glycopeptide Y1 ion in conventional methods can depend on the amino acid sequence of the glycopeptide and its attached glycan structures.

The methods and apparatus of this invention provide surprisingly effective collision energy for fragmentation of different glycopeptides, regardless of their structure.

An embodiment of a dual ion trap mass spectrometer of this invention is shown in FIG. 1. Referring to FIG. 1, the dual ion trap mass spectrometer can have two ionization sources, matrix-assisted laser desorption/ionization (MALDI) and electrospray ionization (ESI). The dual ion trap mass spectrometer can have two ion trap mass analyzers. A first mass analyzer can be a 3D quadruple ion trap (QIT), and a second mass analyzer can be a linear ion tap (LIT).

Referring to FIG. 1, a dual ion trap mass spectrometer of this invention can employ two detection modalities. First, the linear ion trap has a mass-selected radial resonance ejection mode of ion detection. In radial ion ejection, ions can be resonance ejected by supplemental AC applied on two radial rods of the linear ion trap. A detector is located on each side of the linear ion trap in order to collect ions without loss. Second, the linear ion trap has a mass-selected axial resonance ejection mode of ion detection. In this mode, a dipolar excitation RF is applied to XY rods of the linear ion trap. When the kinetic energy of a trapped ion overcomes the fringe field of both end-caps, then the trapped ion is forward ejected to the axial detector.

Detectors for the ion trap can include a conversion dynode and channeltron.

The dual ion trap mass spectrometer of this disclosure can have the two ion traps and the detectors located within a vacuum enclosure.

A sample plate coupled with an x-y stage can be located within the vacuum enclosure for vacuum MALDI. An electrospray source with a pulsed valve can be used to control the flow of ions into quadrupole ion trap. For example, the electrospray ionization source can be modified to include a Parker Pulse Valve Miniature High Speed High Vacuum Dispense Valve. This pulsed valve can be used to create a pulsed ion beam as the ion source.

Automatic Glycopeptide Sequencing

In some embodiments, glycosylation sites and the amino acid sequence of a glycopeptide can be simultaneously identified from a single run of a mass analysis.

Figure 2:
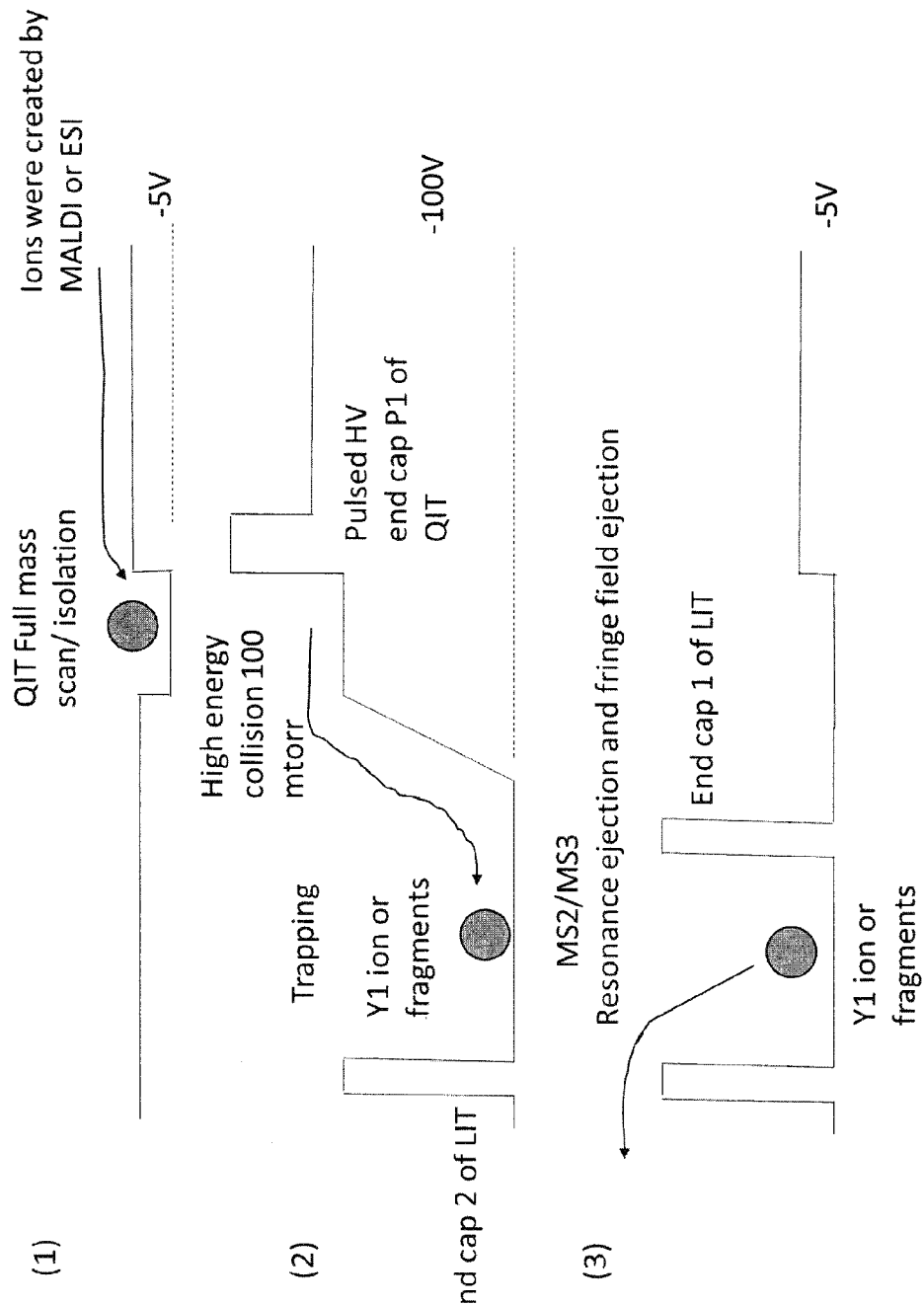
FIG. 2 shows a schematic of an embodiment of a method for obtaining a mass spectrum of a glycopeptide. The method can involve three stages, including collision induced dissociation processes detected with a dual ion trap mass spectrometer. In (1), analyte ions generated by MALDI or ESI are trapped with a quadrupole ion trap. The molecular weights of the analyte ions can be obtained in a full mass scan ($MS^1$). Following this, a selected analyte ion species was isolated in the quadrupole ion trap. In (2), the selected analyte ion species enter a collision and acceleration chamber. The pressure and acceleration in the chamber induces collisions, which create glycopeptide Y1 ions, via higher energy collision dissociation, as well as other glycopeptide fragments. In (3), the glycopeptide Y1 ions and glycopeptide fragments enter a linear ion trap. A mass spectrum $MS^2$ of the glycopeptide Y1 ions and glycopeptide fragments can be obtained by voltage ramp or frequency scan of the linear ion trap. Subsequently, the glycopeptide Y1 ions can be selected and undergo collision induced dissociation. A mass spectrum $MS^3$ of the fragmented glycopeptide Y1 ions can be obtained by voltage ramp or frequency scan of the linear ion trap.

Referring to FIG. 2, in certain embodiments, a three-stage mass spectrum is acquired. The three-stage mass spectrum can include: (1) a full mass range $MS^1$ scan, (2) a higher energy collision dissociation $MS^2$ scan; and (3) a collision induced dissociation $MS^3$ scan.

Referring to FIG. 2, in (1) ions are introduced and trapped in a quadrupole ion trap. Subsequently, target ions are selected by an isolation process in the quadrupole trap. The quadrupole ion trap was floated with DC bias to increase the kinetic energy of the target ions. Target ions are extracted by an applied pulse of positive high voltage on end-cap P1 of the quadrupole ion trap. In (2), the pulsed valve 65 is opened to allow collision gas to fill the collision and acceleration chamber 60, when ions pass through from the quadrupole ion trap to the linear ion trap. The parent and daughter ions, which include Y1 ions, are created by fragmentation in the chamber 60, and then captured by the linear ion trap. In (3), the linear ion trap can be used to perform $MS^2$ mass profiling, which searches Y1 ions, or isolated Y1 ions. The linear ion trap can also be used to perform $MS^3$ tandem mass spectrometry.

The pulsed valve 65 is used to introduce collision gas. Examples of the pulsed valve 65 include a Parker Series 9 Miniature Calibrant Gas Valve. The pulsed valve 65 is a two way normally closed solenoid valve. When 24 VDC or 12 VDC is applied, the valve opens for the duration time of the trigger signal, which is at least 2 ms.

The result of the three-stage mass spectrum obtained in the dual ion trap mass spectrometer of this invention can provide automatic glycopeptide sequencing (AGSY).

The higher energy collision dissociation $MS^2$ scan generates and isolates glycopeptide Y1 ions for the subsequent collision induced dissociation $MS^3$ scan. The glycopeptide Y1 ion contains the un-fragmented peptide sequence plus one GlcNAc residue. The $MS^3$ result in AGSY directly provides the amino acid sequence of the peptide backbone of the glycopeptide. The amino acid sequence of the glycopeptide can be determined by directly searching $MS^3$ data in a database such as Mascot or Sequest.

In addition, the glycosylation site can be determined by the assignment of variable modifications of HexNAc on asparagine from a database search. The amino acid sequence of a glycopeptide can be directly determined from collision induced dissociation $MS^3$ scan data in AGSY, regardless of the presence of non-glycopeptides in the sample. This is because the portion of the $MS^3$ spectrum that is generated from non-glycopeptides will find no peptide match in the database search.

In the methods and apparatus of this invention, automatic determination and isolation of unique glycopeptide Y1 ions in $MS^2$ spectra provide the input for automatic amino acid sequencing of glycopeptides via $MS^3$.

In operation, the signal intensity of glycopeptide Y1 ion peaks can be maximized in order to allow automatic selection of glycopeptide Y1 ions in $MS^2$ spectra.

It has been found that glycopeptide Y1 ions had surprisingly strong signals, the normalized intensities of glycopeptide Y1 ions were 100%, when the normalized collision energies (NCE) were set between 70% and 110%, so long as the m/z detection was limited to be greater than 800. When these conditions were met, the glycopeptide Y1 ion signal in the higher energy collision dissociation $MS^2$ scan did not depend on glycan structure or the charge state of the glycopeptide precursor ion.

Embodiments of this invention can therefore provide, with suitable normalized collision energies, the automatic selection for glycopeptide Y1 ion in the higher m/z region of a higher energy collision dissociation $MS^2$ scan, regardless of the structure of the glycopeptide. This, in turn, allows the determination of the amino acid sequence of the glycopeptide from the collision induced dissociation $MS^3$ scan in an apparatus of this invention having dual ion traps and being capable of employing both fragmentation techniques.

In general, for fragmentation under resonance excitation, the collision efficiency is dependent on m/z. In order to get more efficient fragmentation of high mass molecules, the collision voltage will increase related to m/z. The normalized collision energy is defined as is known in the art. The kinetic energy is set at 100V (floated Paul ion trap), which is 100% high collision energy for m/z 2000. Thus, for example, the normalized collision energy of m/z 200 is 10% as 10V.

For collision dissociation, examples of the collision gas include nitrogen, helium, neon, krypton, argon, or air. The pressure of the collision gas can be from 10-100 mTorr.

Example 1

Model glycopeptides were enzyme digested from bovine fetuin Five N-linked glycopeptides containing the same amino acid sequence LCPDCPLLAPLNDSR (SEQ ID NO: 1), but with different glycan antennary structures, numbers of sialic acids in glycan, and charge states in glycopeptide precursor ions were used.

Figure 3:
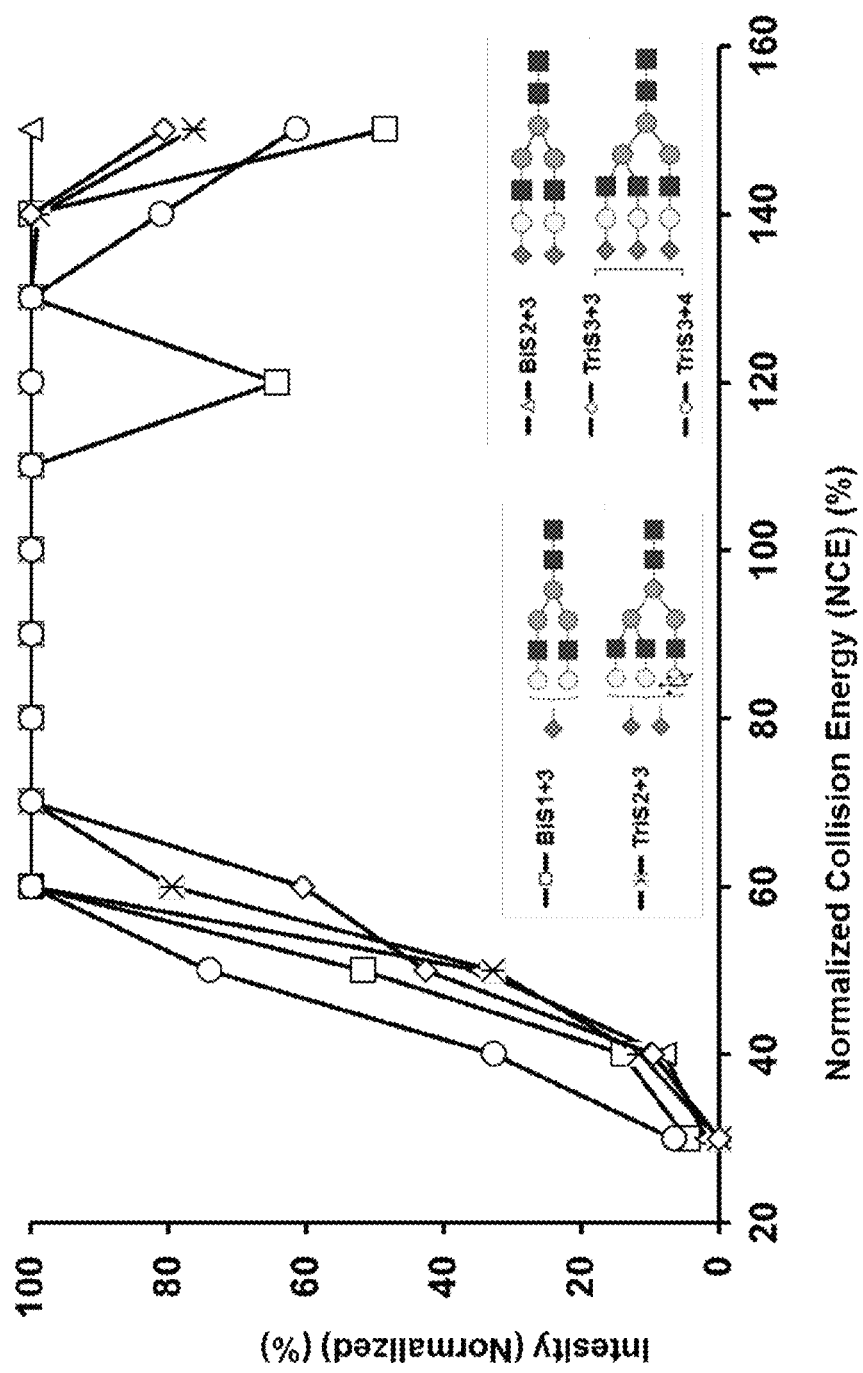
FIG. 3 shows the effect of normalized collision energy on the intensity of glycopeptide Y1 ion signals. The normalized intensity is defined as the peak intensity of glycopeptide Y1 ion over the strongest peak signal in the m/z>800 region.

The signal intensity profiles of glycopeptide Y1 ions were monitored in higher energy collision dissociation $MS^2$ scans, while different normalized collision energies (NCE) were applied. Referring to FIG. 3, the corresponding glycan antennary structures, the numbers of sialic acids, and the charge states of glycopeptides are shown. For example, BiS1+3 represents a triply charged N-type glycopeptide containing a bi-antennary glycan with one sialic acid. Because all five model glycopeptides contain the same amino acid sequence, their glycopeptide Y1 ions were identical in higher energy collision dissociation $MS^2$ mass spectra. FIG. 3 shows that the glycopeptide Y1 ion has the strongest signal when NCE settings are between 70% and 110% in the $MS^2$ spectrum.

Figure 4:
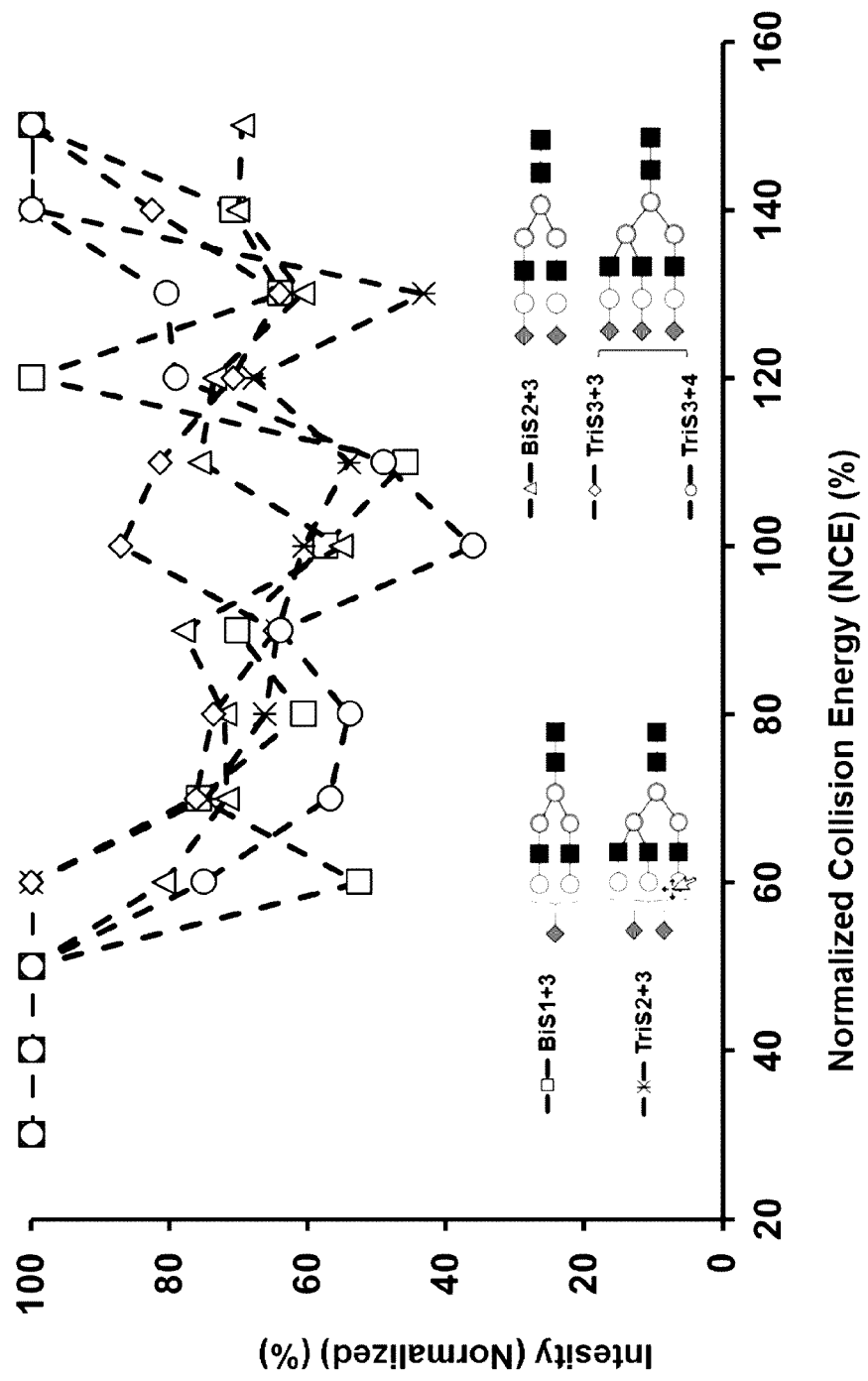
FIG. 4 shows the normalized intensity of the peak which has the strongest signal except Y1 ion as a function of normalized collision energy in m/z>800. All glycopeptides contain the same amino acid peptide sequence, LCPDCPLLAPLNDSR (SEQ ID NO: 1), but with different glycan structures. The figure legend represents the glycan antennary structures, the numbers of sialic acids and the charge states of glycopeptides. For example, BiS1+3 indicates a triply charged glycopeptide with one sialic acid on a bi-antennary glycan structure. The sugar symbols in figure legend are: (■) N-acetyl glucosamine; (○) mannose (open circles); (●) galactose (shaded circles); and (♦) sialic acid.

Signal intensities of fragment ions, except glycan oxonium ions, in the higher m/z region from these $MS^2$ scans were determined. Referring to FIG. 4, FIG. 4 shows the normalized intensity of the peak that has the most abundant signal other than glycopeptide Y1 ion, as a function of the NCE. FIG. 4 shows that peaks other than for the glycopeptide Y1 ion are smaller than that of the glycopeptide Y1 ion. Thus, the strongest signal by far in the higher energy collision dissociation $MS^2$ mass spectra will be the signal for the glycopeptide Y1 ion. This permits automatic selection of the glycopeptide Y1 ion in $MS^2$ for subsequent $MS^3$ detection.

In conventional mass analysis, a typical NCE setting is 30%, and therefore conventional mass analysis could not provide automatic amino acid sequencing of glycopeptides via $MS^3$.

The signal of glycan oxonium ions was avoided by restricting the m/z>800.

Thus, with the appropriate setting of NCE and the restricted detection region of m/z, the signals of glycopeptide Y1 ions surprisingly have the highest intensity of any signals in the $MS^2$ spectra, and can be automatically selected for subsequent $MS^3$ detection in AGSY.

Example 2

Normalized intensities of glycopeptide Y1 ions from an N-linked glycopeptide, LCPDCPLLAPLNDSR (SEQ ID NO: 1) with glycan structure TriS3 were monitored in higher energy collision dissociation $MS^2$ mass spectra. Although this N-linked glycopeptide showed a signal at m/z 1945.31 in $MS^1$ as a triply charged precursor ion, the charge states of double, triple, and quadruple charged ions were manually assigned for monitoring the glycopeptide Y1 ion signal in $MS^2$.

Figure 5:
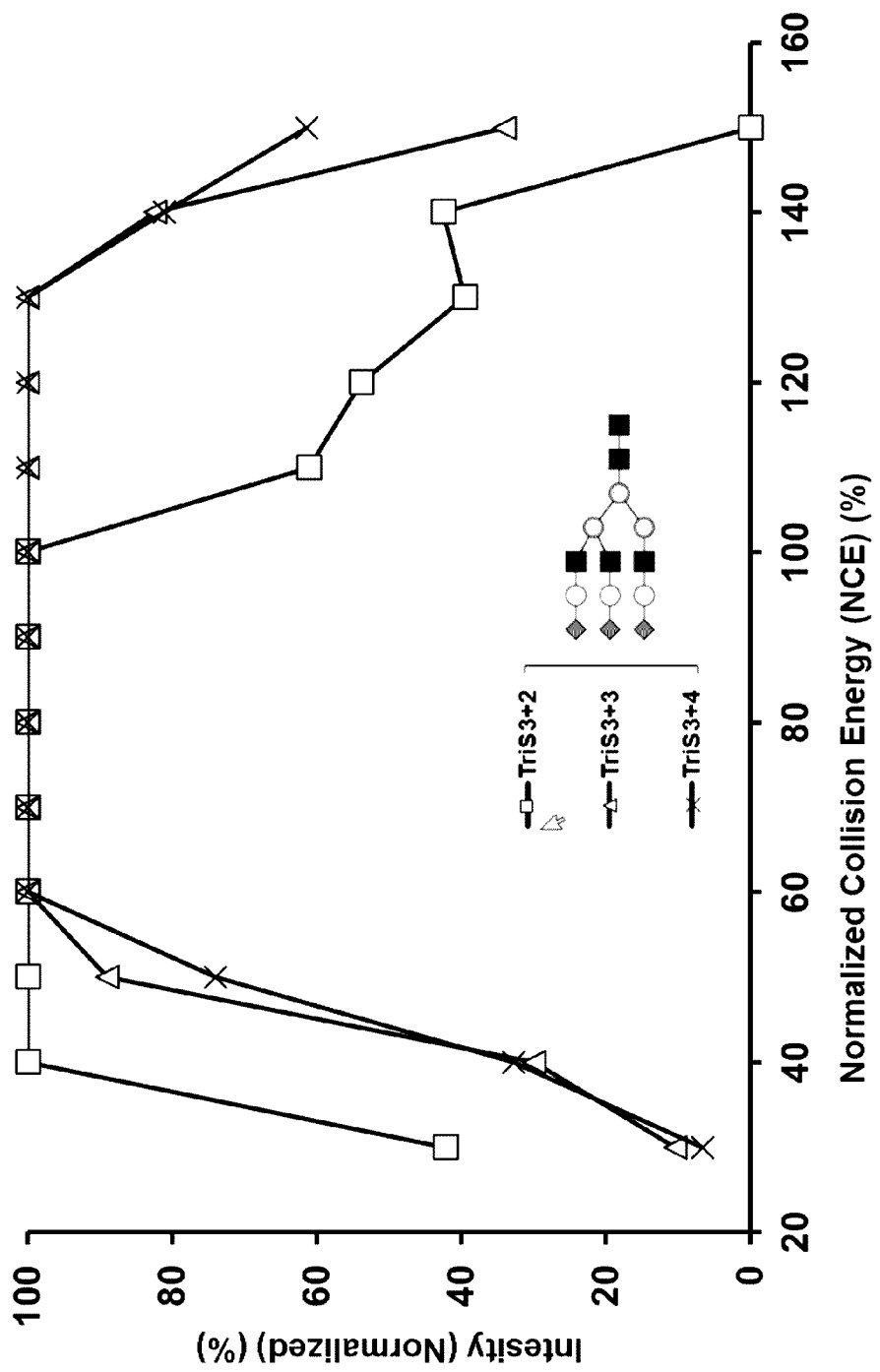
FIG. 5 shows the normalized intensity of the glycopeptide Y1 ion as a function of NCE for doubly, triply, and quadruply charged N-linked glycopeptide LCPDCPLLAPLNDSR (SEQ ID NO: 1) with TriS3 structure for all signals in m/z>800.

Referring to FIG. 5, it was found that glycopeptide Y1 ions surprisingly showed the highest signal intensities in the NCE between 70% and 110%, even though the other precursor ions were observed.

Figure 6:
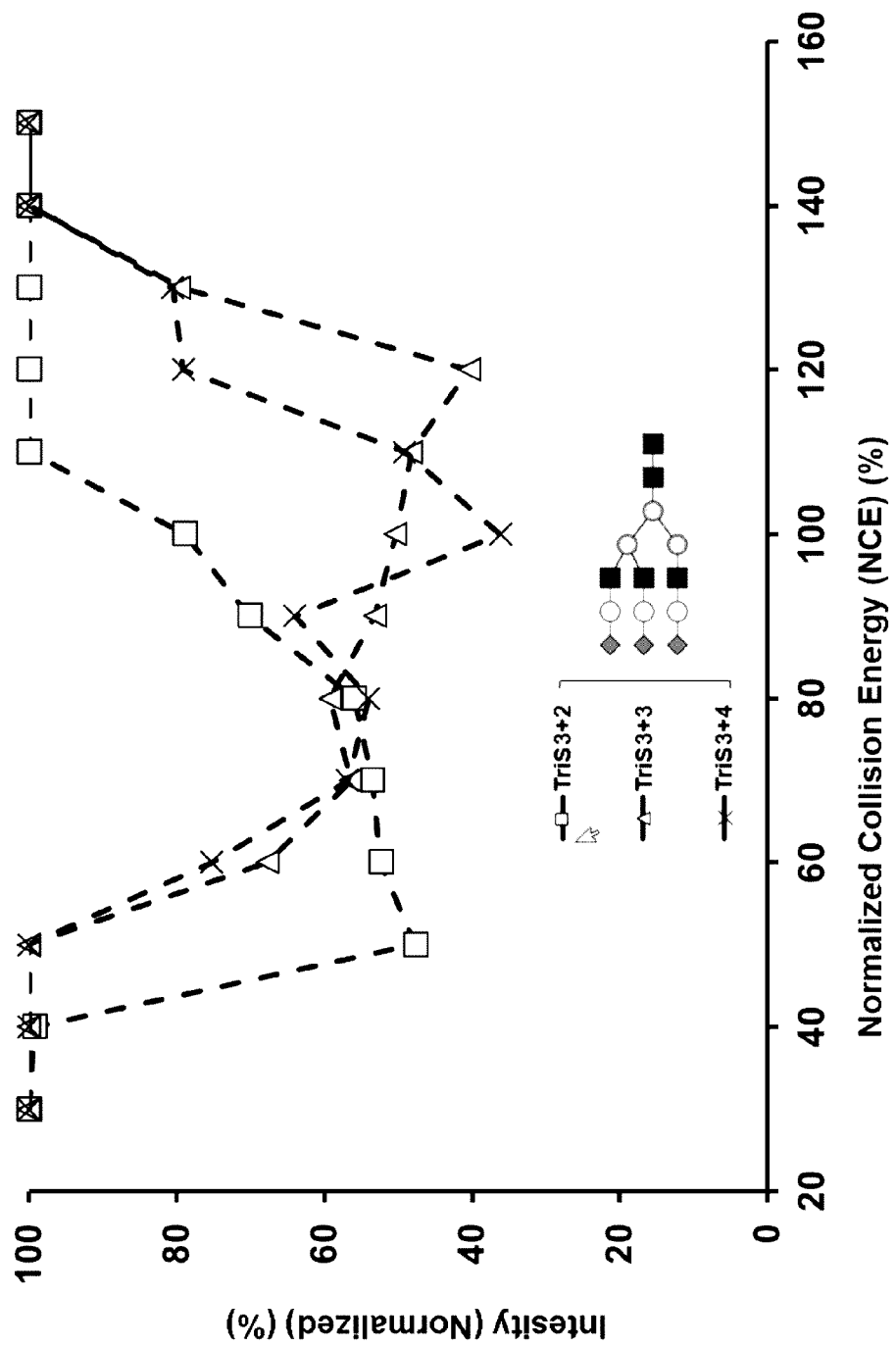
FIG. 6 shows the normalized intensity of peak which has the strongest signal but not the Y1 ion as a function of NCE for doubly, triply, and quadruply charged N-linked glycopeptide LCPDCPLLAPLNDSR (SEQ ID NO: 1) with TriS3 structure for all signals in the mass range of m/z>800. The sugar symbols in figure legend are the same as described in FIG. 1.

Referring to FIG. 6, peaks other than for the glycopeptide Y1 ion are smaller than that of the glycopeptide Y1 ion.

These results show that other charged states of glycopeptide precursor ions in $MS^1$ spectrum have no significant effect on the determination of glycopeptide Y1 ion in $MS^2$. Thus, the automatic selection of glycopeptide Y1 ion from $MS^2$ spectra in AGSY can be performed with a dual ion trap mass spectrometer at relatively low mass resolution.

Example 3

Three model glycoproteins including bovine fetuin, human 1-acid glycoprotein, and horseradish peroxidase were used to demonstrate AGSY. Glycoproteins were treated by a double enzyme digestion system (trypsin and chymotrypsin) to increase the protein sequence coverage.

Peptides from digested glycoproteins were directly analyzed with a dual ion trap mass spectrometer by AGSY, without performing any glycopeptide enrichment procedure. The identified N- and O-linked glycosylation sites of bovine fetuin, human 1-acid glycoprotein, and horseradish peroxidase are summarized in Tables 1 to 3, respectively.

Figure 7:
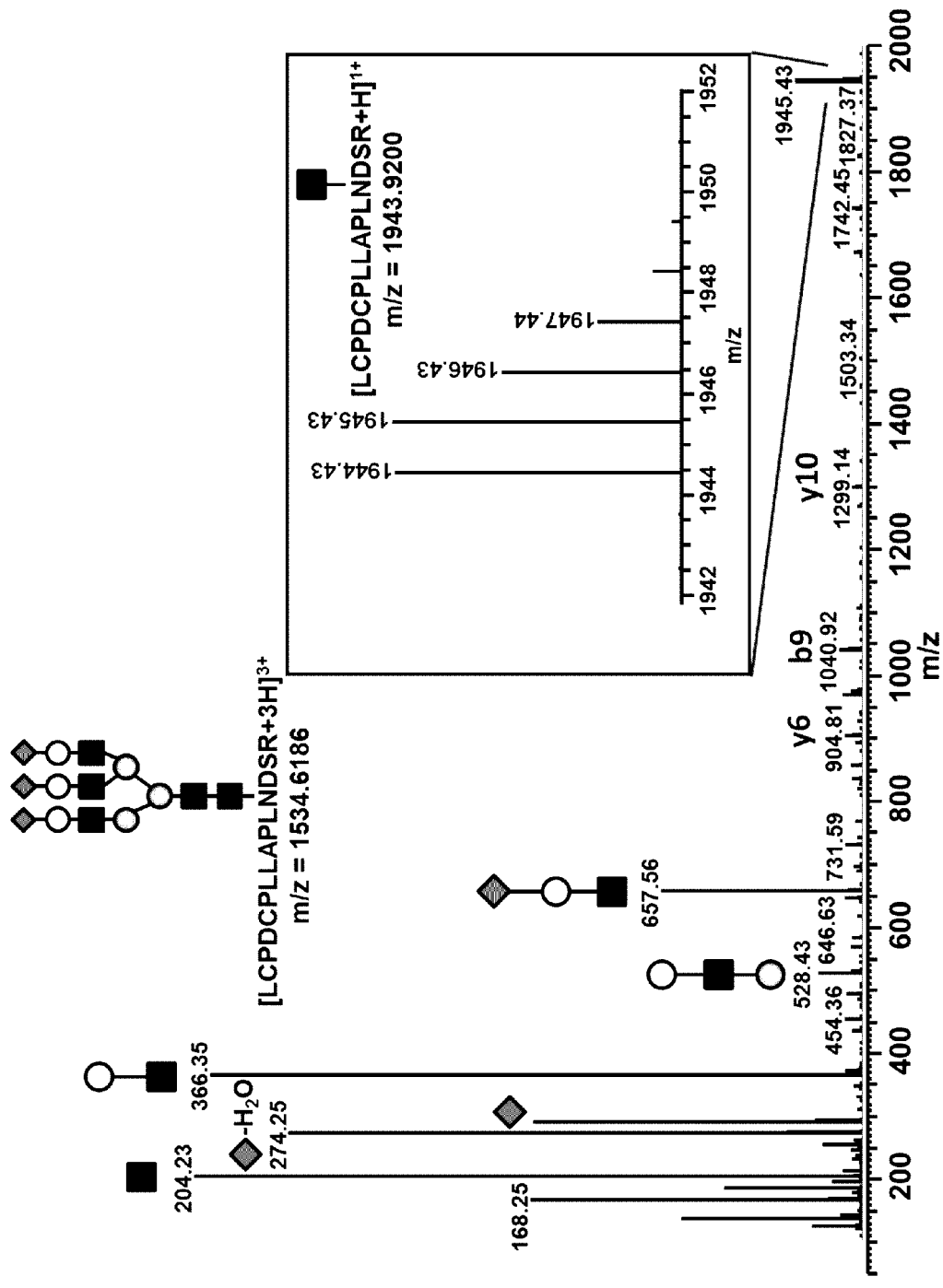
FIG. 7 shows the $MS^2$ mass spectrum of an N-linked glycopeptide, $^{146}$LCPDCPLLAPLNDSR$^{160}$ (SEQ ID NO: 1). The $MS^2$ spectrum was obtained after higher energy collision dissociation fragmentation. The glycopeptide Y1 ion is the strongest signal in m/z>800. The glycopeptide Y1 ion was automatically selected for a subsequent collision induced dissociation fragmentation scan ($MS^3$). The oxonium ions of glycopeptides are shown in m/z region less than 400.
Figure 8:
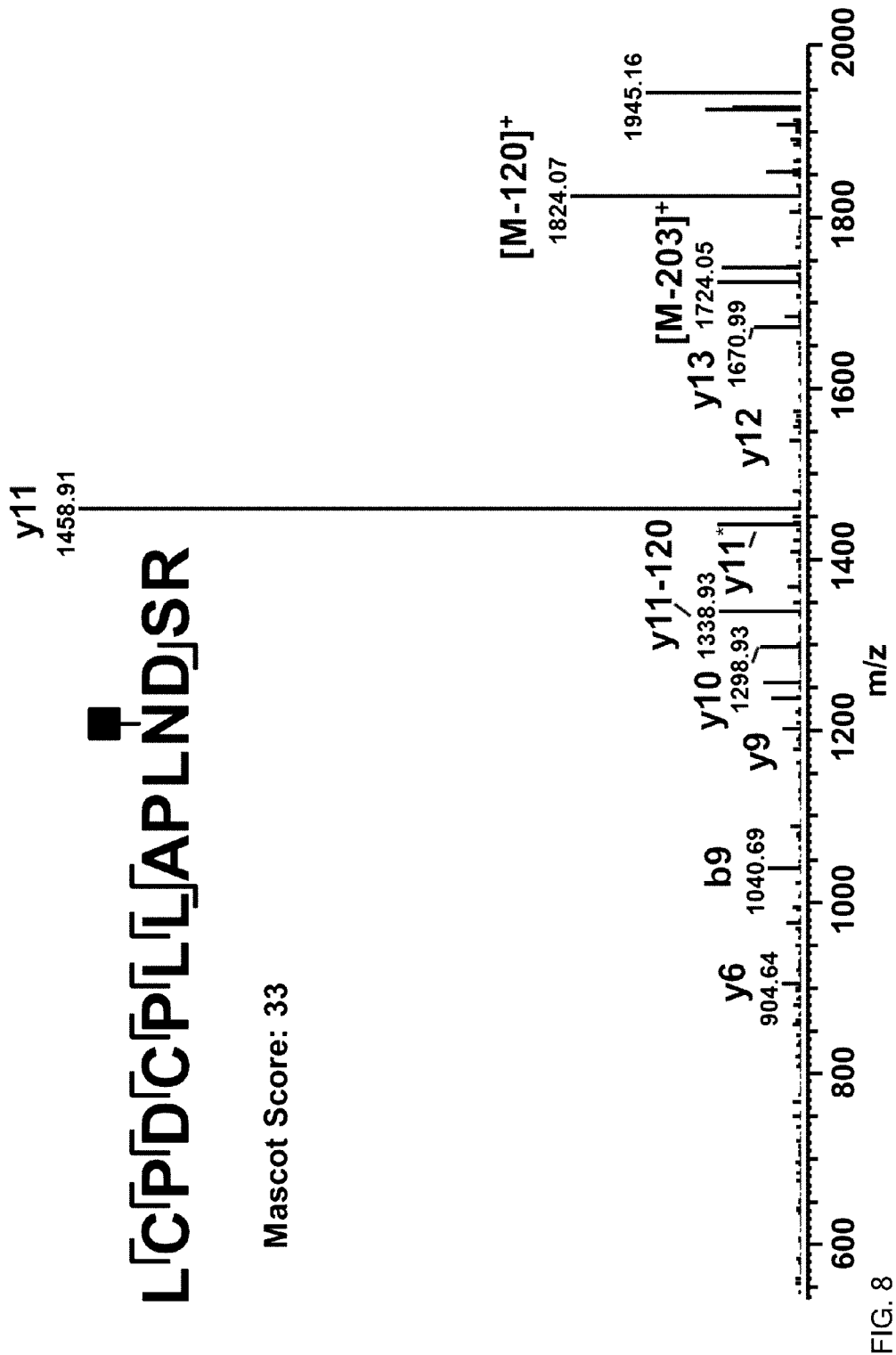
FIG. 8 shows the $MS^3$ mass spectrum of an N-linked glycopeptide, $^{146}$LCPDCPLLAPLNDSR$^{160}$ (SEQ ID NO: 1). The $MS^3$ spectrum was obtained after collision induced dissociation fragmentation of the glycopeptide Y1 ion. The amino acid sequence of the glycopeptide can be directly determined from a search of peak listing of CID-$MS^3$ spectra in the Mascot database.

The $MS^2$ and $MS^3$ spectra of an N-linked glycopeptide, a tryptic peptide from bovine fetuin A with sequence of LCPDCPLLAPLNDSR (SEQ ID NO: 1) and TriS3 glycan, are shown in FIGS. 7 and 8, respectively. Referring to FIG. 7, the $MS^2$ spectrum was obtained from the selection of a triply charged precursor ion at m/z 1535 in the $MS^1$ survey scan, followed by the HCD fragmentation. The glycopeptide Y1 ion, a singly charged signal at m/z 1944 in the HCD $MS^2$, has the highest signal intensity in the m/z range greater than 800 when NCE was set to 70%.

Referring to FIG. 8, the glycopeptide Y1 ion (m/z 1944) was automatically selected for the subsequent CID-$MS^3$ acquisition. The peak list converted from this $MS^3$ spectrum was directly submitted for MS/MS analysis in Mascot with HexNAc specified as the variable modification. The amino acid sequence and the glycosylation site of this N-type glycopeptide, LCPDCPLLAPLNDSR (SEQ ID NO: 1), were then correctly determined by this $MS^3$ data with the Mascot score.

Example 4

Figure 9:
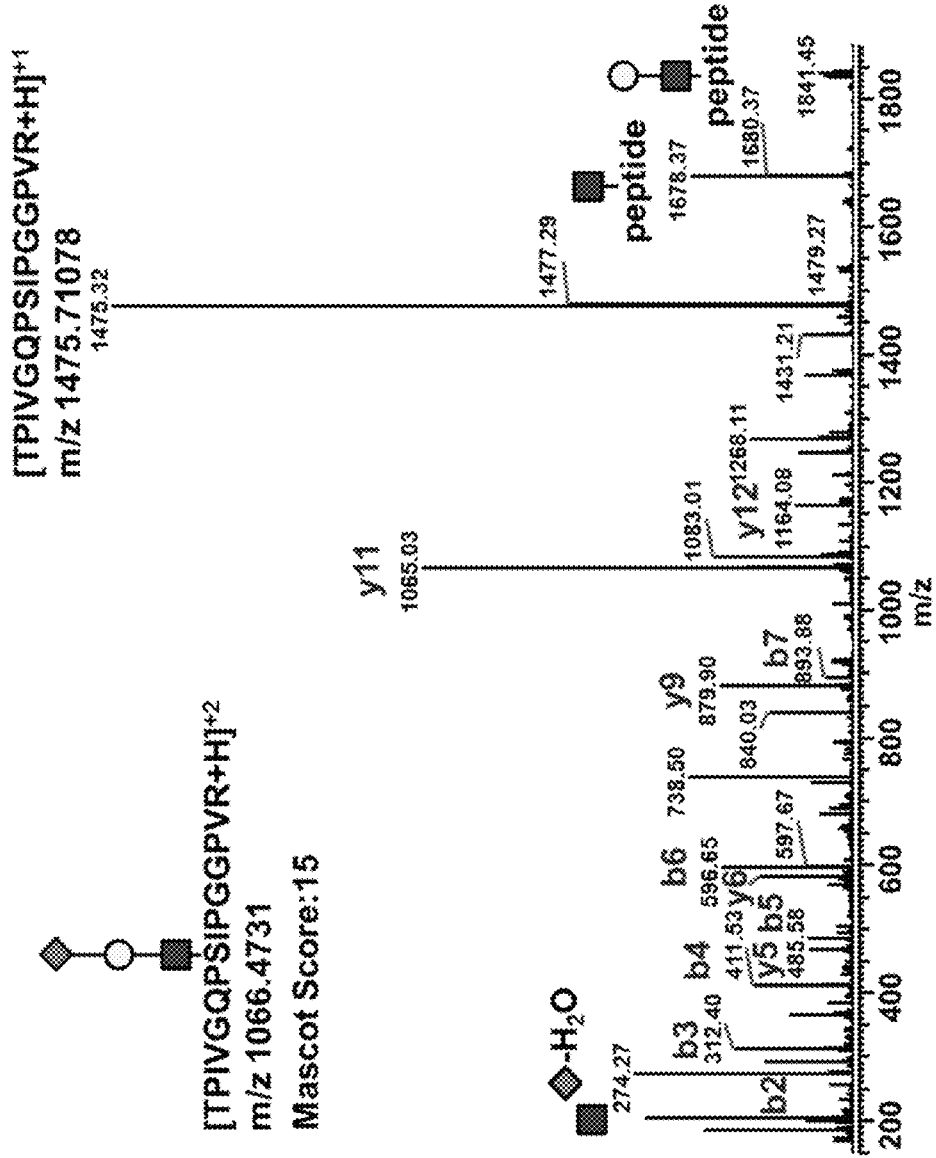
FIG. 9 shows the $MS^2$ mass spectrum of an O-linked glycopeptide $^{334}$TPIVGQPSIPGGPVR$^{348}$ (SEQ ID NO: 2). The $MS^2$ spectrum was obtained after higher energy collision dissociation fragmentation. The glycopeptide Y1 ion shows the most intensive signal in m/z>800. The glycopeptide Y1 ion was automatically selected for a subsequent collision induced dissociation fragmentation scan ($MS^3$). The product ion signals observed in the $MS^2$ spectrum are from the fragmentation of peptide backbone of the O-linked glycopeptide.
Figure 10:
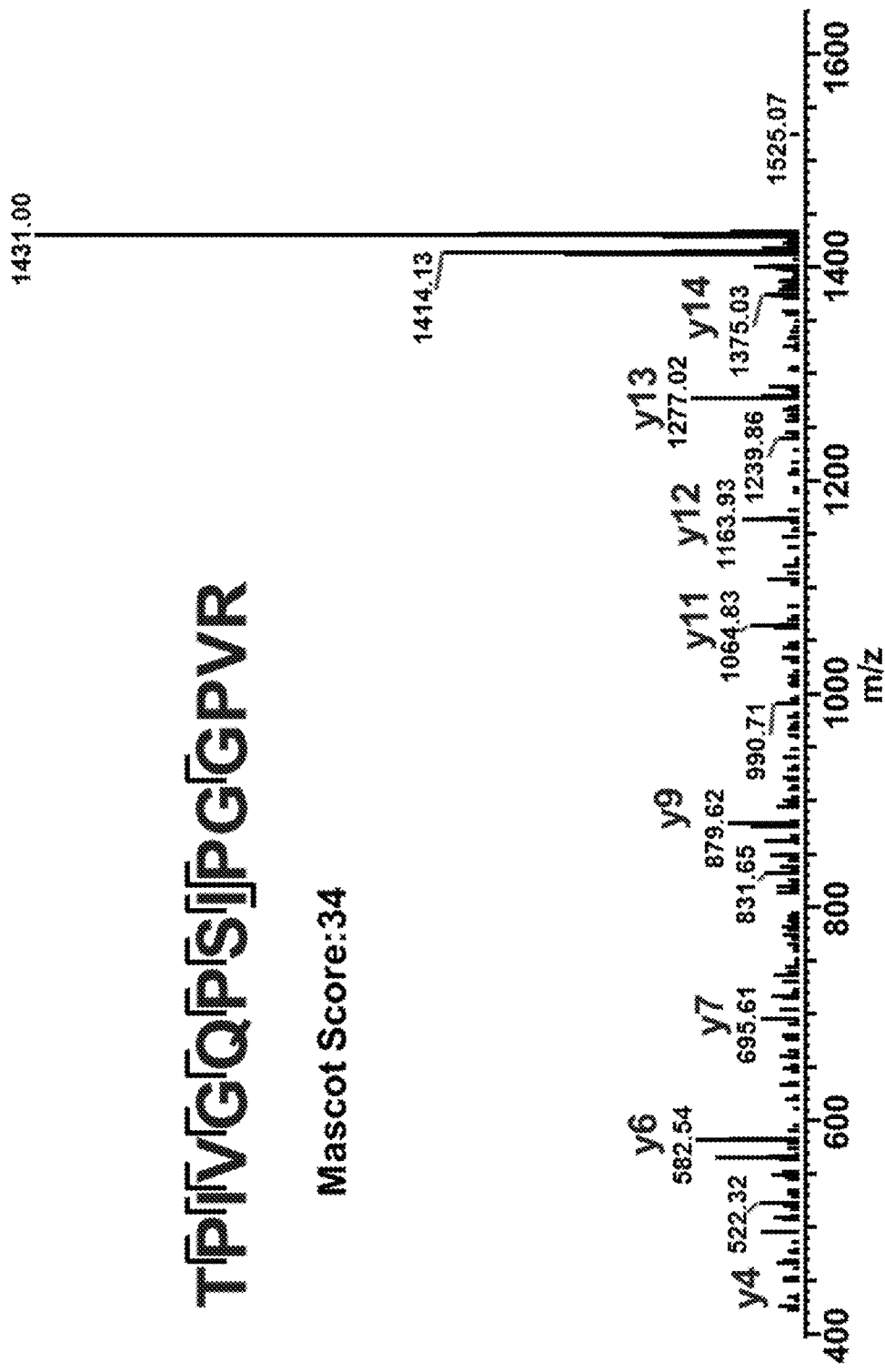
FIG. 10 shows the $MS^3$ mass spectrum of an O-linked glycopeptide $^{334}$TPIVGQPSIPGGPVR$^{348}$ (SEQ ID NO: 2). The $MS^3$ spectrum was obtained after collision induced dissociation fragmentation of the glycopeptide Y1 ion. The amino acid sequence of the glycopeptide can be directly determined from a search of peak listings of CID-$MS^3$ spectra in Mascot database.

The NCE value determined for N-linked glycopeptides in Example 3 was found to be operable for O-linked glycopeptides. Referring to FIG. 9, the identification of an O-linked glycopeptide, TPIVGQPSIPGGPVR (SEQ ID NO: 2), was performed by AGSY. This glycopeptide was from trypsin digested bovine fetuin A and contained an O-type glycan, HexNAc-Hex-Sialic Acid, on serine. The most abundant signal of this O-linked glycopeptide after HCD fragmentation in $MS^2$ spectrum was at m/z 1475 (FIG. 9), which was generated from a doubly charged precursor ion at m/z 1066 in the $MS^1$ survey scan. Using the same procedure for N-linked glycopeptide identification, the peak list converted from the CID-$MS^3$ spectrum (FIG. 10) was submitted to Mascot with HexNAc modification and the amino acid sequence of the O-linked glycopeptide was determined by Mascot with the score of 34.

Unlike glycopeptides with N-type glycan, the strongest signals of O-linked glycopeptides in the $MS^2$ spectrum were peptide ions, instead of the glycopeptide Y1 ions. Because glycosidic bonds may be easily broken in collision induced fragmentation, the chemical linkages between HexNAc to either serine or threonine in O-linked glycopeptides have similar properties with glycosidic bonds in glycan. Thus, the formation of peptide ions for O-linked glycopeptides in AGSY by HCD induced $MS^2$ is frequently observed.

These results show that $MS^2$ and $MS^3$ spectra from N- and O-linked glycopeptides can be used for analysis and sequencing of the glycopeptides. The signal in the $MS^2$ spectrum used for the subsequent $MS^3$ may arise from glycopeptide Y1 ion (N-type glycopeptide) or peptide ion (O-type glycopeptide). However, in either case, the amino acid sequence of the glycopeptides can always be determined from the subsequent CID-$MS^3$.

In addition to signals generated from the fragmentation of the peptide backbone, the product ion signals from the destruction of glycan in $MS^2$ and $MS^3$ spectra were also observed. These signals were utilized as the signature peaks to confirm the presence of glycopeptide in AGSY.

For example, a sequential sugar loss from the O-linked glycopeptide was observed in HCD $MS^2$ spectrum, including the loss of one sialic acid (−291, m/z 1841), one Hex (−162, m/z 1678), and one HexNAc (−203, m/z 1475), as shown in FIG. 9.

Moreover, the Y1—120 (0,2X) and Y1—203 (loss of one GlcNAc) at m/z 1824 and 1742 in the CID-MS3 spectrum of an N-linked glycopeptide, LCPDCPLLAPLNDSR (SEQ ID NO: 1), were also found in FIG. 8. When model glycoproteins were examined by AGSY, a new O-type glycosylation site, T295 of bovine fetuin B (Table 1), and a new N-type glycosylation site, N316 of horseradish peroxidase (Table 3), were identified. Glycopeptides including these two newly discovered glycosylation sites were automatically sequenced by AGSY; in addition, the glycan oxonium ions identified in both HCD induced MS² spectra further confirmed these findings.

When model glycoproteins were examined by AGSY, a new O-type glycosylation site, T295 of bovine fetuin B (Table 1), were identified. Glycopeptides including these two newly discovered glycosylation sites were automatically sequenced by AGSY; in addition, the glycan oxonium ions identified in both HCD induced MS2 spectra further confirmed these findings.

TABLE 1

Glycopeptides and their corresponding glycoforms identified by AGSY for trypsin/chymotrypsin double enzyme digestion of bovine fetuin (FETUA_BOVIN)

| Site[1] | Peptide sequence | Glycan[2] | Precursor ion[3] | Ion (type)[4] | Mascot score[5] | Peak area[6] |
|---|---|---|---|---|---|---|
| N99 | ANCSVR (SEQ ID NO: 3) | H6N5S3 | 1191(3+) | 909(Y1) | 11 | 19220000 |
| | | H6N5S4 | 1288(3+) | 909(Y1) | 6 | 10161000 |
| | DPTPLANCSVR (SEQ ID NO: 4) | H6N5S3 | 1365(3+) | 1432(Y1) | 24 | 18346000 |
| N156 | LAPLNDSR (SEQ ID NO: 5) | H5N2S2 | 1547(2+) | 1089(Y1) | 15 | 36714000 |
| | | H5N4S2 | 1032(3+) | 1089(Y1) | 8 | 65380000 |
| | | H6N5S1 | 1056(3+) | 1089(Y1) | 8 | 6047600 |
| | | H6N5S2 | 1153(3+) | 1089(Y1) | 20 | 83543000 |
| | | | 1729(2+) | | 8 | 13812000 |
| | | H6N5S3 | 1250(3+) | 1089(Y1) | 22 | 206810000 |
| | | | 1875(2+) | | 12 | 20289000 |
| | | H6N5S4 | 1347(3+) | 1089(Y1) | 14 | 41196000 |
| | CPDCPLLAPLNDSR (SEQ ID NO: 6) | H5N4S2 | 960(4+) | 1831(Y1) | 33 | 24682000 |
| | | H5N7S3 | 1184(4+) | 1831(Y1) | 31 | 285540000 |
| | | H6N5S2 | 1051(4+) | 1831(Y1) | 47 | 29514000 |
| | | | 1401(3+) | | 36 | 20512000 |
| | | H6N5S3 | 1124(4+) | 1831(Y1) | 36 | 122450000 |
| | LCPDCPLLAPLNDSR (SEQ ID NO: 1) | H5N4S1 | 1219(3+) | 1944(Y1) | 40 | 23748000 |
| | | H5N4S2 | 989(4+) | 1944(Y1) | 51 | 65920000 |
| | | | 1316(3+) | | 57 | 305890000 |
| | | H5N4S3 | 1413(3+) | 1944(Y1) | 39 | 14289000 |
| | | H5N5S2 | 1385(3+) | 1944(Y1) | 28 | 11831000 |
| | | H6N5S1 | 1341(3+) | 1944(Y1) | 19 | 29703000 |
| | | H6N5S2 | 1079(4+) | 1944(Y1) | 23 | 100180000 |
| | | | 1438(3+) | | 49 | 171460000 |
| | | H6N5S3 | 1152(4+) | 1944(Y1) | 49 | 498810000 |
| | | | 1535(3+) | | 59 | 403660000 |
| | | H6N5S4 | 1225(4+) | 1944(Y1) | 44 | 60479000 |
| | | | 1633(3+) | | 45 | 16732000 |
| N176 | NAESNGSYL (SEQ ID NO: 7) | H6N5S3 | 1273(3+) | 1157(Y1) | 7 | 211660000 |
| | | H6N5S4 | 1371(3+) | 1157(Y1) | 13 | 42476000 |
| | NAESNGSYLQLVEISR (SEQ ID NO: 8) | H6N5S2 | 1089(4+) | 1982(Y1) | 23 | 32222000 |
| | | | 1452(3+) | | 17 | 32980000 |
| | | H6N5S3 | 1162(4+) | 1982(Y1) | 64 | 73880000 |
| | | | 1549(3+) | | 55 | 51944000 |
| | | H6N5S4 | 1235(4+) | 1982(Y1) | 8 | 7922300 |
| S341 | TPIVGQPSIPGGPVR (SEQ ID NO: 2) | H1N1S1 | 1065(2+) | 1475(peptide) | 72 | 197090000 |

TABLE 1-continued

Glycopeptides and their corresponding glycoforms identified by AGSY for trypsin/chymotrypsin double enzyme digestion of bovine fetuin (FETUA_BOVIN)

| Site[1] | Peptide sequence | Glycan[2] | Precursor ion[3] | Ion (type)[4] | Mascot score[5] | Peak area[6] |
|---|---|---|---|---|---|---|
| N271 | GE<u>N</u>ATVNQRPANPSK (SEQ ID NO: 9) | H6N5S2 | 1039(4+) | 1787(Y1) | 8 | 3332500 |
|  |  | H6N5S3 | 1112(4+) | 1787(Y1) | 56 | 15546000 |
|  |  | H6N5S4 | 1184(3+) | 1787(Y1) | 7 | 7626200 |
| T295[7] | TEELQQQNTAP<u>T</u>NSPTK (SEQ ID NO: 10) | H1N1S1 | 1273(2+) | 1888(peptide) | 111 | 22256000 |

Note 1:
The known glycosylation sites for bovine fetuin A (FETUA_BOVIN) are N99, N156, N176, S271, T280, S282, S341 (http://www.uniprot.org/uniprot/P12763), and for bovine fetuin B (FETUB_BOVIN) are N37, N137, N271 (http://www.uniprot.org/uniprot/Q58D62).

Note 2:
The glycan compositions were determined by subjecting the molecular weight of each glycan to GlycoWorkBench[34] followed by manually assignment. The one letter code for sugars are, H: hexose, N: HexNAc, F: deoxyhexose, P: pentose, and S: sialic acid.

Note 3:
The precursor ions and their charge states identified in MS for the consequent HCD MS[2].

Note 4:
The signal selected in HCD MS[2] and their types (glycopeptide Y1 ions or peptide ions) for the subsequent CID-MS[3].

Note 5:
The highest Mascot search score from CID-MS[3] spectra of each glycopeptide.

Note 6:
Peak areas are determined based on XIC by using MASIC[35].

Note 7:
A new identified O-type glycosylation site by AGSY in bovine fetuin B.

TABLE 2

Glycopeptides and their corresponding glycoforms identified by AGSY for trypsin/chymotrypsin double enzyme digestion of human $\alpha_1$-acid glycoprotein (A1AG1_HUMAN)

| Site[1] | Peptide sequence | Glycan[2] | Precursor ion[3] | Ion (type)[4] | Mascot score[5] | Peak area[6] |
|---|---|---|---|---|---|---|
| N33 | CANLVPVPIT<u>N</u>ATLDR (SEQ ID NO: 11) | H6N6F1S2 | 1540(3+) | 1958(Y1) | 25 | 4256500 |
|  |  |  | 1155(4+) |  | 26 | 6083800 |
|  |  | H7N6S2 | 1192(4+) | 1958(Y1) | 26 | 5402800 |
|  |  |  | 1588(3+) |  | 32 | 8680100 |
|  |  | H8N3S4 | 1588(3+) | 1958(Y1) | 32 | 8680100 |
| N56 | NEEY<u>N</u>K (SEQ ID NO: 12) | H6N5S3 | 1220(3+) | 999(Y1) | 7 | 1287600 |
|  |  | H6N5F1S3 | 1269(3+) | 999(Y1) | 1 | 36540000 |
| N72 | YFTP<u>N</u>KTEDTIFLR (SEQ ID NO: 13) | H7N6S2 | 1172(4+) | 1949(Y1) | 39 | 2838300 |
|  |  | H7N6S3 | 1245(4+) | 1949(Y1) | 55 | 5764600 |
|  |  | H7N6S4 | 1317(4+) | 1949(Y1) | 44 | 4138200 |
| N93 | QDQCIY<u>N</u>TTYL<u>N</u>VQR (SEQ ID NO: 14) | H5N5S3 | 1521(3+) | 1916 (peptide) | 22 | 3032600 |
|  |  | H6N6S3 | 1642(3+) | 1916 (peptide) | 33 | 9973300 |
|  |  | H6N6F1S1 | 1123(4+) | 1916 (peptide) | 34 | 9429300 |
|  |  |  | 1497(3+) | (peptide) | 56 | 14812000 |
|  |  | H6N6F1S2 | 1593(3+) | 1916 (peptide) | 38 | 40835000 |
|  |  |  | 1196(4+) | (peptide) | 44 | 71765000 |
|  |  | H6N6S4 | 1306(4+) | 1916 (peptide) | 30 | 1935700 |
|  |  | H6N6F2S4 | 1378(4+) | 1916 (peptide) | 23 | 10938000 |
|  |  | H7N7F1S1 | 1619(3+) | 1916 (peptide) | 36 | 11898000 |

TABLE 2-continued

Glycopeptides and their corresponding glycoforms identified by AGSY for trypsin/chymotrypsin double enzyme digestion of human α₁-acid glycoprotein (A1AG1_HUMAN)

| Site[1] | Peptide sequence | Glycan[2] | Precursor ion[3] | Ion (type)[4] | Mascot score[5] | Peak area[6] |
|---|---|---|---|---|---|---|
| | | H7N7F1S2 | 1716(3+) | 1916 (peptide) | 35 | 13303000 |
| | | | 1287(4+) | (peptide) | 42 | 73931000 |
| | | H7N7F1S3 | 1360(4+) | 1916 (peptide) | 10 | 22764000 |
| N103 | ENGTISR (SEQ ID NO: 15) | H7N6S3 | 1262(3+) | 979(Y1) | 1 | 28838000 |
| | | H7N6S4 | 1075(4+) | 979(Y1) | 3 | 19532000 |
| | | H7N6F1S4 | 1481(4+) | 979(Y1) | 1 | 17558000 |

Note 1:
The known glycosylation sites for human α₁-acid glycoprotein (A1AG1_HUMAN) are N33, N56, N72, N93, and N103 (http://www.uniprot.org/uniprot/P02763).

When model glycoproteins were examined by AGSY, a new O-type glycosylation site, T295 of bovine fetuin B (Table 1), and a new N-type glycosylation site, N316 of horseradish peroxidase (Table 3), were identified. Glycopeptides including these two newly discovered glycosylation sites were automatically sequenced by AGSY; in addition, the glycan oxonium ions identified in both HCD induced MS2 spectra further confirmed these findings.

TABLE 3

Glycopeptides and their corresponding glycoforms identified by AGSY for trypsin/chymotrypsin double enzyme digestion of horseradish peroxidase (PER1A_ARMRU)

| Site[1] | Peptide sequence | Glycan[2] | Precursor ion[3] | Ion (type)[4] | Mascot score[5] | Peak area[6] |
|---|---|---|---|---|---|---|
| N43 | YDNSCPNVSNIVR (SEQ ID NO: 16) | H2N3P1 | 850(3+) | 1741(Y1) | 10 | 86318000 |
| | | H3N3P1 | 903(3+) | 1741(Y1) | 21 | 235800000 |
| | | | 1355(2+) | | 12 | 76719000 |
| | DNSCPNVSNIVR (SEQ ID NO: 17) | H2N3P1 | 1193(3+) | 1578(Y1) | 5 | 45274000 |
| N87 | LDNTTSFRTEKDAFGNANSAR (SEQ ID NO: 18) | N2 | 908(3+) | 1260(Y1)(2+) | 30 | 141610000 |
| | | N1F1 | 889(3+) | 1260(Y1)(2+) | 24 | 230710000 |
| | | N2F1 | 957(3+) | 1260(Y1)(2+) | 37 | 291740000 |
| | | H2N2 | 1017(3+) | 1260(Y1)(2+) | 18 | 112110000 |
| | | H2N2F1P1 | 1109(3+) | 1260(Y1)(2+) | 29 | 99558000 |
| | | H3N2F1 | 1119(3+) | 1260(Y1)(2+) | 36 | 117050000 |
| | | H3N2F1P1 | 873(4+) | 1260(Y1)(2+) | 38 | 5264600000 |
| | | | 1163(3+) | | 28 | 586780000 |
| | | H3N3F1P1 | 923(4+) | 1260(Y1)(2+) | 43 | 367380000 |
| | | H4N2F1P1 | 913(4+) | 1260(Y1)(2+) | 35 | 954550000 |
| | LDNTTSFR (SEQ ID NO: 19) | H2N2 | 843(2+) | 1157(Y1) | 9 | 56535000 |
| | | H2N2P1 | 909(2+) | 1157(Y1) | 9 | 64404000 |
| | | H2N2F1P1 | 981(2+) | 1157(Y1) | 9 | 192690000 |
| | | H3N2F1 | 997(2+) | 1157(Y1) | 8 | 186480000 |
| | | H3N2F1P1 | 1063(2+) | 1157(Y1) | 10 | 5412800000 |
| | | H3N3F1P1 | 1165(2+) | 1157(Y1) | 10 | 205560000 |
| | | H4N2F1P1 | 1144(2+) | 1157(Y1) | 9 | 793480000 |
| N188 | DSFRNVGLNRSSDLVAL (SEQ ID NO: 20) | H3N2F1P1 | 1012(3+) | 1034(Y1)(2+) | 11 | 274960000 |
| | NVGLNRSSDLVAL (SEQ ID NO: 21) | H1N2F1 | 1037(2+) | 1561(Y1) | 5 | 28107000 |
| | | H3N2F1P1 | 844(3+) | 1561(Y1) | 9 | 96816000 |

TABLE 3-continued

Glycopeptides and their corresponding glycoforms identified by AGSY for trypsin/chymotrypsin double enzyme digestion of horseradish peroxidase (PER1A_ARMRU)

| Site[1] | Peptide sequence | Glycan[2] | Precursor ion[3] | Ion (type)[4] | Mascot score[5] | Peak area[6] |
|---|---|---|---|---|---|---|
| N285 | GLIQSDQELFSSPNATDTIPLVR (SEQ ID NO: 22) | H3N2F1P1 | 1837(2+) | 1353(Y1)(2+) | 68 | 211230000 |
|  | FSSPNATDTIPLVR (SEQ ID NO: 23) | H3N2F1P1 | 897(3+) | 1721(Y1) | 26 | 57969000 |
|  | SSPNATDTIPLVR (SEQ ID NO: 24) | N1F1 | 861(2+) | 1370(peptide) | 50 | 853280000 |
|  |  | N2 | 889(2+) | 1573(Y1) | 34 | 358730000 |
|  |  | N2F1 | 962(2+) | 1573(Y1) | 36 | 291190000 |
|  |  | H1N2 | 970(2+) | 1370(peptide) | 48 | 240960000 |
|  |  | H1N2F1 | 1044(2+) | 1573(Y1) | 25 | 116770000 |
|  |  | H2N2P1 | 1117(2+) | 1573(Y1) | 26 | 104330000 |
|  |  | H2N2F1 | 1125(2+) | 1573(Y1) | 33 | 132580000 |
|  |  | H3N2P1 | 1199(2+) | 1573(Y1) | 26 | 278500000 |
|  |  | H3N2F1 | 1205(2+) | 1573(Y1) | 26 | 108490000 |
|  |  | H3N2F1P1 | 848(3+) | 1573(Y1) | 37 | 3015800000 |
|  |  |  | 1272(2+) |  | 30 | 3442100000 |
|  | FSSPNATDTIPLVR (SEQ ID NO: 23) | H3N2F1P1 | 897(3+) | 1721(Y1) | 27 | 57969000 |
| N316 | VEAMDRMGNITPLTGTQGQIR (SEQ ID NO: 25) | H3N2P1 | 1105(3+) | 1247(Y1)(2+) | 41 | 13277000 |
|  | MGNITPLTGTQGQIR (SEQ ID NO: 26) | H3N2P1 | 1307(2+) | 1790(Y1) | 8 | 86318000 |

Note 1:
The known glycosylation sites for horseradish peroxidase (PER1A_ARMRU) are N43, N87, N188, N216, N228, N244, N285, and N298 (http://www.uniprot.org/uniprot/P00433).
Note 2:
A new identified N-type glycosylation site by AGSY.

Example 5

Monitoring the Glycoform Changes in Biological Samples

In addition to identifying the glycosylation sites in proteins, AGSY also provides qualitative and quantitative information of various glycoforms for each glycosylation site. When glycopeptides containing the same amino acid sequence, but with different corresponding glycoforms, were analyzed by AGSY, they showed identical MS$^3$ spectra, because of the same precursor ions from either glycopeptide Y1 ions (for N-linked glycopeptides) or peptide ions (for O-linked glycopeptides) in MS$^2$. Thus, the molecular weights of the corresponding glycans can be calculated from their precursor ions in MS$^1$, and the amino acid sequence of glycopeptide can be determined from the MS$^3$ result.

The molecular weight of glycan was then subjected to GlycoWorkBench for resolving its sugar composition. However, the additional manual assignment was required for determining the correct sugar composition for each glycan because the molecular weights of glycans were obtained with relatively low mass accuracy data using the dual ion trap mass spectrometer of this invention. The AGSY method utilized the extract ion chromatograms (XIC) of glycopeptides, and integrated with MASIC35 for glycan quantitation.

The conventional glycan quantitation method was based on the release of all glycans with a fluorephore label, e.g. 2-aminobenzamide (2-AB), followed by liquid chromatographic separation coupled with the fluorescent or mass spectrometry detection. It provided the overall glycan quantity profile for glycoprotein, but not for individual glycosylation sites.

The AGSY method of this invention can distinguish the quantities of different glycoforms for each glycosylation site in glycoproteins. Although the quantitative comparison between glycopeptides and non-glycopeptides is not practical due to the lower ionization efficiency of glycopeptides than non-glycopeptides, the relative quantitation for various glycoforms by the AGSY method can provide useful information such as monitoring the glycoform changes in biological samples.

Tables 1 to 3 summarize the N- and O-type glycosylation sites that were identified by AGSY in bovine fetuin, human a1-acid glycoprotein, and horseradish peroxidase, respectively. These three model glycoproteins were selected for representing different types of glycans. Bovine fetuin demonstrated the general glycan structures with typical sugar compositions. Human a1-acid glycoprotein and horseradish peroxidase mainly contain deoxyhexose (fucose) and pentose in glycans, respectively.

The data in Tables 1 to 3 demonstrated that the AGSY method can identify most previously reported glycosylation sites in three model glycoproteins. Further, AGSY can determine sugar compositions as well as their relative quantities for each glycan based on the assumption of similar ionization efficiency for glycopeptides with similar glycan structures.

For example, TriS3, TriS2, and BiS2 were determined to be the major types of glycan structures in bovine fetuin by AGSY, and TriS3 was the most abundant glycoform (Table 1). This result is consistent with the conclusion from previous studies. Glycoform changes in the same glycosylation site may completely alter biological properties of glycoprotein. Some of these changes can be related to the tumorigenesis process. Therefore, the quantitative comparison between different glycoforms on the same glycosylation site is very important in biological application.

All publications and patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A mass spectrometer apparatus for glycopeptide analysis comprising:
   an ionization source for creating glycopeptide analyte ions;
   a quadrupole ion trap;
   a linear ion trap;
   a collision chamber between the quadrupole ion trap and the linear ion trap;
   a pulsed valve for introducing a collision gas into the collision chamber through an elongated tube to provide a high density molecular beam to collide with the glycopeptide analyte ions; and
   a detector;
   wherein mass-selected glycopeptide analyte ions exit the quadrupole ion trap into the collision chamber, thereby forming glycopeptide Y1 ions and product ions, and wherein the linear ion trap performs mass analysis of glycopeptide Y1 ions and product ions created by higher energy collision dissociation fragmentation or collision induced dissociation fragmentation of the glycopeptide analyte ions that have exited the quadrupole ion trap;
   wherein the higher energy collision dissociation fragmentation has a normalized collision energy from 70% to 110%, based on 100 V kinetic energy as being 100% high collision energy for an m/z of 2000 and pressure of the collision gas from 10-100 mTorr.

2. The mass spectrometer apparatus of claim 1, wherein the ion source includes MALDI and ESI sources.

3. The mass spectrometer apparatus of claim 1, wherein the ion source includes an ESI source with a pulsed beam.

4. The mass spectrometer apparatus of claim 1, including an ion guide between the ion source and the quadrupole ion trap.

5. The mass spectrometer apparatus of claim 1, wherein the quadrupole ion trap is a mass analyzer.

6. The mass spectrometer apparatus of claim 1, wherein the linear ion trap is a mass analyzer.

7. A method for automatic amino acid sequencing of a glycopeptide, the method comprising:
   obtaining the full mass range mass spectrum of glycopeptide analyte ions in a quadrupole ion trap;
   selecting target glycopeptide ions from the full mass range mass spectrum and isolating the target glycopeptide ions in the quadrupole ion trap;
   introducing a collision gas at a pressure from 10 to 100 mTorr into the collision chamber through a pulsed valve and through an elongated tube to provide a high density molecular beam to collide with the glycopeptide analyte ions;
   fragmenting the target glycopeptide ions by higher energy collision dissociation fragmentation, thereby obtaining fragmented glycopeptide analyte ions and glycopeptide Y1 ions;
   obtaining the mass spectrum of the fragmented glycopeptide analyte ions and glycopeptide Y1 ions in the linear ion trap, thereby identifying the glycopeptide Y1 ions;
   isolating the glycopeptide Y1 ions in the linear ion trap;
   fragmenting the glycopeptide Y1 ions in the linear ion trap by collision induced dissociation fragmentation;
   obtaining the mass spectrum of the fragmented glycopeptide Y1 ions in the linear ion trap, thereby providing mass spectral peaks corresponding to the amino acid sequence of the glycopeptide;
   wherein the higher energy collision dissociation fragmentation has a normalized collision energy from 70% to 110%, based on 100 V kinetic energy as being 100% high collision energy for an m/z of 2000.

8. The method of claim 7, wherein the mass range of the linear ion trap is set to m/z greater than 800.

9. The method of claim 7, further comprising analyzing the mass spectral peaks corresponding to the amino acid sequence of the glycopeptide for a matching structure in a database of collision induced dissociation mass spectra.

10. The method of claim 7, wherein the glycopeptide is an O-linked glycopeptide or an N-linked glycopeptide.

11. The method of claim 7, wherein the linear ion trap is operable for mass analysis by voltage scan and frequency scan.

12. A method for determining the glycoform of a glycopeptide, the method comprising:
   obtaining the $MS^1$ mass spectrum of glycopeptide precursor ions in a mass spectrometer according to claim 1;
   introducing a collision gas at a pressure from 10 to 100 mTorr into the collision chamber of the mass spectrometer through a pulsed valve and through an elongated tube to provide a high density molecular beam to collide with the glycopeptide precursor ions;
   fragmenting the glycopeptide precursor ions by higher energy collision dissociation fragmentation to obtain glycopeptide product ions, wherein the higher energy collision dissociation fragmentation has a normalized collision energy from 70% to 110%, based on 100 V kinetic energy as being 100% high collision energy for an m/z of 2000;
   obtaining the $MS^3$ mass spectrum of glycopeptide product ions in a mass spectrometer according to claim 1;
   determining the amino acid sequence of the glycopeptide from the $MS^3$ mass spectrum;
   determining the molecular weights of the glycans of the glycopeptide from the glycopeptide precursor ions and the determined amino acid sequence.

13. The method of claim 12, including resolving the sugar composition of the glycopeptide from the determined molecular weights of the glycans.

* * * * *